United States Patent [19]

Fries et al.

[11] Patent Number: 5,360,612

[45] Date of Patent: Nov. 1, 1994

[54] PHARMACEUTICAL COMPOSITIONS CONTAINING TRIAZOLE DERIVATIVES FOR RECTAL ADMINISTRATION

[75] Inventors: Walter F. Fries; Günther F. D. Pfaff; Jörg C. Pfitzner; Gerhard Simon, all of Illertissen, Germany

[73] Assignee: Pfizer Inc., New York, N.Y.

[21] Appl. No.: 959,869

[22] Filed: Oct. 13, 1992

[51] Int. Cl.$^5$ .......................... A01N 55/02; A61F 9/02
[52] U.S. Cl. ......................... 424/436; 424/DIG. 15; 514/383; 514/384; 514/965; 514/966
[58] Field of Search ............... 514/383, 384, 965, 966; 424/436, DIG. 15

[56] References Cited

U.S. PATENT DOCUMENTS

| | | | |
|---|---|---|---|
| 4,870,092 | 9/1989 | Elbe et al. | 514/383 |
| 4,960,782 | 10/1990 | Gymer et al. | 514/383 |
| 4,992,454 | 2/1991 | Richardson | 514/383 |

Primary Examiner—Thurman K. Page
Assistant Examiner—Carlos Azpuru
Attorney, Agent, or Firm—Peter C. Richardson; Paul Ginsburg; Garth Butterfield

[57] ABSTRACT

This invention relates to pharmaceutical compositions for rectal administration containing semi-synthetic glycerides produced by interesterification, and, as the active ingredient, triazole derivatives of the formula

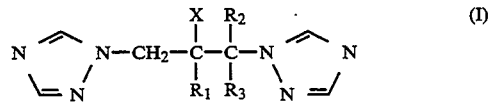

wherein $R^1$ is phenyl optionally sustituted with from one to three substituents independently selected from the group consisting of F, Cl, Br, I, $CF_3$, $(C_1-C_4)$alkyl, $(C_1-C_4)$alkoxy, and 5-chloropyrid-2-yl; X is OH, F, Cl or Br; $R_2$ is $H_2$, $CH_3$ or F; and $R_3$ is H or F.

12 Claims, No Drawings

PHARMACEUTICAL COMPOSITIONS CONTAINING TRIAZOLE DERIVATIVES FOR RECTAL ADMINISTRATION

BACKGROUND OF THE INVENTION

A problem with therapeutically active substances is that these compounds cannot be administered by every administration route at the same dosage level with the same resulting activity. Various substances which can be injected show a considerable loss of activity on oral administration. Other substances, which can be orally administered, lose bioavailability to a considerable extent if they are rectally administered.

Oral administration forms are particularly problematical in those patients who tend to vomit. This problem is apparent with therapies such as immunosuppression or candidiasis of the oesophagus.

Administration in the form of injections is not appropriate in many cases. Many people have a fear of frequent injections and with cachectic patients injection is difficult. The present invention is therefore intended to provide rectally administered pharmaceutical compositions which have approximately the same bioavailability of active component as oral administration forms.

In order to achieve the same high blood level values as after an oral dose, approximately a 1.5 to 3 to fold amount of the oral dose must be incorporated in the suppository (H. Sucker, P. Fuchs and R. Speiser, Pharmazeutishe Technologie (Pharmaceutical Technology), Georg Thieme Verlag, Stuttgart 1978). The problem of incorporating a substantially higher amount of the active compound is that absorption can differ greatly from person to person and in the case of good absorption a blood level value is achieved which is clearly above the optimum blood level value.

It is therefore the object of the present invention to make available a pharmaceutical composition for rectal administration which has approximately the same bioavailability as an oral administration form.

SUMMARY OF THE INVENTION

A pharmaceutical composition for rectal administration is therefore disclosed which comprises the following constituents:

a) at least one therapeutically active triazole compound of the general formula:

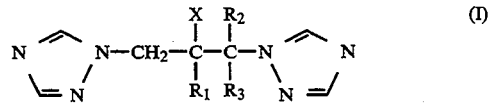

wherein $R_1$ is phenyl optionally substituted with from one to three substituents independently selected from the group consisting of F, Cl, Br, I, $CF_3$, $(C_1-C_4)$alkyl, $(C_1-C_4)$alkoxy, and 5-chloropyrid-2-yl;

X is OH, F, Cl or Br;

$R_2$ is H, $CH_3$ or F;

and $R_3$ is H or F;

and wherein the triazole derivative being employed comprises an amount of 0.1 to 25 percent by weight, preferably 1 to 10 percent by weight, relative to the total weight of the composition, and b) semi-synthetic glycerides, composed of saturated fatty acid glycerides having a chain length of $C_8$ to $C_{18}$, and having a melting range of 32°–44° C., preferably in the range of 35°–39° C., and wherein the semi-synthetic glycerides comprise between to 80 to 99.9 percent by weight, relative to the total weight of the pharmaceutical composition, and c) a mixture of solid, purified, saturated hydrocarbons having a solidification point of 40°–70° C., in particular of 50°–62° C., wherein the hydrocarbons comprise between 0 to 8 percent by weight, relative to the total weight of the pharmaceutical composition.

The composition may, moreover, contain auxiliaries customary in suppositories to a small extent.

The therapeutically active constituents of the above pharmaceutical compositions are triazole derivatives which have antimycotic activity. Compounds of formula I and methods for their syntheses are described in U.S. Pat. No. 4,404,216, which is hereby incorporated by reference in its entirety.

In a preferred embodiment, the triazole derivatives of formula I have the general formula (II):

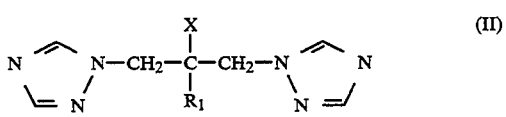

wherein $R_1$ is phenyl optionally substituted with from 1 to 3 substituents independently selected from the group consisting of F, Cl, Br, I and $CF_3$, and wherein X is OH, F, Cl or Br.

In particularly preferred embodiments, the triazole derivative of formula I is 1,3-bis(1H-1,2,4-triazol-1-yl)-2-bromo-2-(2,4-dichlorophenyl)propane, 1,3-bis(1H-1,2,4-triazol-1-yl)-2-chloro-2-(2,4-dichlorophenyl)propane or 1,3-bis(1H-1,2,4-triazol-1-yl)-2-(4-iodophenyl)-propan-2-ol.

The most preferred triazole derivative is 2,4-difluoro-α,α-bis(1H-1,2,4-triazol-1-ylmethyl)benzyl alcohol (fluconazole).

DETAILED DESCRIPTION OF THE INVENTION

One or more different triazole derivatives can be incorporated into the pharmaceutical compositions claimed.

A therapuetically effective dose of 25–400 mg of the triazole derivative of formula I per individual administration form (suppository) is preferably employed. This active compound is only soluble to a very small extent in the rectal fluid, which is customarily about 1–3 ml.

Quantitatively, the main constituent of the pharmaceutical compositions according to the invention is the semi-synthetic glycerides (b). The semi-synthetic glycerides employed according to the invention are composed of saturated fatty acid glycerides having a chain length of the fatty acids of 6 to 20 carbon atoms. In a preferred embodiment, the chains of the fatty acids have 8 to 18 carbon atoms.

The iodine number of the semi-synthetic glycerides is preferably below 3 and particularly preferably below 2.

The hydroxyl number of the semi-synthetic glycerides is preferably below 20 and particularly preferably below 6.

In particularly preferred embodiment, semi-synthetic glycerides are employed which have been prepared by transesterification (interesterification). As a result of this preparation process, lower molecular weight fatty acids are also obtained, which contribute to the "softener" properties. In mixed products of suitable esters and alcohols and also in semi-synthetic glycerides which have been prepared by esterification and not by transesterification, these low molecular weight fatty acids are not present.

According to the invention, semi-synthetic glycerides are employed with fatty acid radicals having 8–18 carbon atoms and which were produced by interesterification.

The semi-synthetic glycerides as used according to the invention can be produced by an interesterification of refined hydrogenated vegetable oils at high temperature using an alkaline reacting catalyst. Alkali soaps can then be removed by rinsing and the product can be decolorized, deodorized and dried.

The semi-synthetic glycerides obtained by interesterification show a more continuous differential scanning calorimeteric melting diagram than the diagram obtained by using materials as described in the prior art (Gstirner, Einführung in die Verfahrenstechnik der Arzneiformung, Wissenschaftliche Verlagsgesellschaft MbH Stuttgart, 1973 (152-155)). The diagram of the semi-synthetic glycerides obtained by interesterification shows only one broad peak whereas the material as used in the prior art shows at least two separate peaks.

The effect of the semi-synthetic glycerides employed according to the invention was compared with the effect of such suppository base materials usually used as adeps solidus and consisting of a mixture of mono-, di- and triglycerides of the saturated fatty acids $C_{11}H_{23}COOH$ to $C_{17}H_{35}COOH$ (Gstirner, "Einfuhrung in die Vertahrentechnik der Arzneiformung", Wissenschaftliche Verlagsgesellschaft mbH, Stuttgart, 1973, p. 152-155). In this comparative test, suppositories were produced which in each case contained the same ratio of a triazole derivative to glycerides. The chain length of the fatty acid radicals of the comparative formulation was in the range between $C_{10}$–$C_{18}$.

In animal experiments with rabbits the parameter AUC (area under the curve), i.e., the area under the plasma level-time curve, and $C_{max}$, i.e., the maximum plasma level concentration, were determined. The following results were obtained:

| Suppositories Basis | Area Under the Curve (mcg × h/ml) | Maximum Concentration $C_{max}$ (mcg/ml) |
| --- | --- | --- |
| semi-synthetic glycerides $C_8$–$C_{18}$ (according to the invention) | 447.3 | 48.06 |
| semi-synthetic glycerides $C_{10}$–$C_{18}$ (according to the Gstirner) | 378.3 | 37.63 |

The table above shows that by using the ($C_8$–$C_{18}$) semi-synthetic glycerides according to the invention, about 18% more of the effective agent was reabsorbed from the suppositories and that the maximum obtainable blood level of the effective substance of this preparation is about 27% higher than by using a mixture of mono-, di- and triglycerides wherein the chain length is between $C_{10}$ and $C_{18}$.

A further constituent of the pharmaceutical composition according to the invention are the solid, purified, saturated hydrocarbons (c), which are employed in an amount of 0 to 8 percent by weight, preferably 2 to 5.5 percent by weight, relative to the total weight of the pharmaceutical composition.

These hydrocarbons have a solidification point of 40°–70° C. and preferably between 50°–62° C. These hydrocarbons are used in the preparation as a viscosity-increasing substance to prevent sedimentation of the active compound. A relatively high viscosity of the melt would be expected to delay the partition and reduce the absorption of the active component on melting of the suppository in the rectum. Surprisingly, this was not observed in the bioavailability investigations. In fact, rapid release of the active compound was observed.

Rapid release of an active compound from a suppository is only expected by one skilled in the art if the oil/water partition coefficient is small. Only then can acceptable bioavailability by expected. For the compound preferably employed (fluconazole), the oil/water partition coefficient has a value of 1.605 and is thus in the middle range of the customary values. Thus, good bioavailability would not be expected.

If solubility/partition values are plotted against one another, the value for fluconazole is close to that for morphine, codeine and ephedrine bases. These compounds, however, do not show good bioavailability from suppository fatty bases. A poor bioavailability therefore also has to be taken into account for a pharmaceutical composition which contains a triazole derivative.

Surprisingly, it has now been found that the triazole derivatives employed according to the invention have a bioavailability which is comparable with oral administration forms if the pharmacologically active compound having a particle size of below 150$\mu$ is suspended in a solidified melt of semi-synthetic glycerides on their own or preferably with the addition of a mixture of solid, purified, saturated hydrocarbons.

In addition to the customary casting in metal moulds, the casting of the suppositories can also be carried out directly in preshaped containers made of plastic, aluminum or plastic laminate.

The present invention is further illustrated with reference to the following examples:

EXAMPLE 1

10 kg of ground 2,4-difluoro-$\alpha,\alpha$-bis(1H-1,2,4-triazol-2-ylmethyl)benzyl alcohol (fluconazole) were added with stirring to a molten mixture of 180.12 kg of semi-synthetic glycerides and 4.88 kg of purified, saturated hydrocarbons. The suspension was homogenized and poured into the appropriate packagings in suppository form. The packagings can be prepared from plastic, aluminum or a laminated material.

EXAMPLE 2

5 kg of 2,4-difluoro-$\alpha,\alpha$-bis(1H-1,2,4-triazol-1-ylmethyl)benzyl alcohol were added with stirring to a molten mixture of 180.25 kg of semi-synthetic glycerides and 9.75 kg of purified, saturated hydrocarbons. The suspension was homogenized and poured into metal moulds in suppository form.

EXAMPLE 3

10 kg of 2,4-difluoro-$\alpha,\alpha$-bis(1H-1,2,4-triazol-1-ylmethyl)benzyl alcohol were added with stirring to a melt of 360 kg of semi-synthetic glycerides. After homogenization, the suspension was poured into metal moulds.

EXAMPLE 4

2.5 kg of 2,4-difluoro-$\alpha,\alpha$-bis(1H-1,2,4-triazol-1-ylmethyl)benzyl alcohol were added with stirring to a molten mixture of 92.56 kg of semi-synthetic glycerides and 2.44 kg of purified, saturated hydrocarbons. The suspension was homogenized and poured into suppository moulds.

EXAMPLE 5

20 kg of 2,4-difluoro-α,α-bis(1H-1,2,4-triazol-1-ylmethyl)benzyl alcohol were added with stirring to a molten mixture of 170.1 kg of semi-synthetic glycerides and 4.9 kg of purified, saturated hydrocarbons. The suspension was homogenized and poured into suppository moulds.

EXAMPLE 6

(Comparative Example)

The pharmacokinetics of suspension and suppositories were compared in a cross-over test in humans.

As active compound, fluconazole was employed in an amount of 25 mg once as suppositories (prepared according to Example 4) and once as suspension. The suspension employed for the comparison contained the following constituents in addition to the active compound: sucrose, colloidal silica, xanthan gum, buffer substances, preservative, colorant and flavoring. The parameters "area under the curve" and $C_{max}$ were determined. The bioavailability of the pharmaceutical forms is assessed with reference to the parameters AUC (area under the curve=area under the plasma level-time curve) and $C_{max}$ (maximum plasma level concentration). The following results were obtained here:

| PARAMETER | SUPPOSITORY | SUSPENSION |
|---|---|---|
| Area under the curve 0–96 h | | |
| (mcg × h/ml) | 19.87 ± 3.2 | 18.58 ± 3.03 |
| $C_{max}$ (mcg/ml) | 0.451 ± 0.062 | 0.544 ± 0.101 |

EXAMPLE 7

(Comparative Example)

The comparison tests according to Example 6 were also carried out using a higher fluconazole concentration. In this case, 200 mg of the active compound were incorporated firstly into the suppositories according to the invention (prepared according to Example 5) and on the other hand incorporated into capsules for oral administration. In addition to the active compound, the comparatively tested capsules contained the following further constituents: lactose, maize starch, colloidal silica, magnesium stearate and sodium lauryl sulphate. The following results were obtained in this case:

| PARAMETER | SUPPOSITORY | CAPSULES |
|---|---|---|
| Area under the curve 0–96 h | | |
| (mcg × h/ml) | 151.3 ± 31 | 163 ± 26 |
| $C_{max}$ | 3.4 ± 0.5 | 3.9 ± 0.5 |
| 1½ (h) | 32.0 ± 6.8 | 33.0 ± 7.8 |

The comparison experiments show that the pharmaceutical preparations according to the invention for rectal administration have the same bioavailability as oral administration forms which have the same concentration of active compound as the suppositories.

We claim:

1. A pharmaceutical composition for rectal administration that comprises the following constituents:
   a) at least one therapeutically active triazole compound of the formula:

$$\begin{array}{c} X \quad R_2 \\ | \quad | \\ N \diagup \diagdown N-CH_2-C-C-N \diagup \diagdown N \\ \diagdown = N \diagup \quad | \quad | \quad \diagdown N = \diagup \\ \quad R_1 \; R_3 \end{array} \quad (I)$$

wherein $R_1$ is phenyl radical optionally substituted with one to three substituents independently selected from the group consisting of F, Cl, Br, I, $CF_3$, $(C_1-C_4)$alkyl, $(C_1-C_4)$alkoxy, and 5-chloropyrid-2-yl;
   X is OH, F, Cl or Br;
   $R^2$ is H, $CH_3$ or F;
   $R^3$ is H or F; and
   wherein the compound of formula I comprises an amount of 0.1 to 25 percent by weight, relative to the total weight of the composition, and
   b) semi-synthetic glycerides produced by interesterification, consisting of saturated fatty acid glycerides having a chain length of $C_8$ to $C_{18}$ and having a melting range of 32°–44° C., wherein the semi-synthetic glycerides comprise between 80 to 99.9 percent by weight, relative to the total weight of the pharmaceutical composition, and
   c) a mixture of solid, purified, saturated hydrocarbons having a solidification point of 40°–70° C., wherein the hydrocarbons comprise between 0 to 8 percent by weight, relative to the total weight of the pharmaceutical composition.

2. A pharmaceutical composition according to claim 1, wherein the therapeutically active agent (a) is a triazole derivative of the following formula (II):

$$\begin{array}{c} X \\ | \\ N \diagup \diagdown N-CH_2-C-CH_2-N \diagup \diagdown N \\ \diagdown = N \diagup \quad | \quad \diagdown N = \diagup \\ \quad R_1 \end{array} \quad (II)$$

wherein $R_1$ is phenyl optionally substituted with from 1 to 3 substituents independently selected from a group consisting of F, Cl, Br, I and $CF_3$ and X is OH, F, Cl or Br.

3. A pharmaceutical composition according to claim 1, wherein the triazole derivative (a) is 1,3-bis(1H-1,2,4-triazol-1-yl)-2-bromo-2-(2,4-dichlorophenyl) propane.

4. A pharmaceutical composition according to claim 1, wherein the triazole derivative (a) is 1,3-bis(1H-1,2,4-triazol-1-yl)-2-chloro-2-(2,4-dichlorophenyl) propane.

5. A pharmaceutical composition according to claim 1, wherein the triazole derivative (a) is 1,3-bis(1H-1,2,4-triazol-1-yl)-2-(4-iodophenyl)propan-2-ol.

6. A pharmaceutical composition according to claim 1, wherein the triazole derivative (a) is 2,4-difluoro-α,α-bis(1H-1,2,4-triazol-1-ylmethyl)benzyl alcohol.

7. A pharmaceutical preparation according to claim 1, wherein the pharmaceutical preparation is present in the form of a suppository for rectal administration, which contains 10–400 mg of the triazole derivative (a) per suppository.

8. A pharmaceutical preparation according to claim 6, wherein the pharmaceutical preparation is present in the form of a suppository for rectal administration, which contains 10–400 mg of the triazole derivative (a) per suppository.

9. A pharmaceutical preparation according to claim 1 wherein the semi-synthetic glycerides (b) have an iodine number of less than 3, and a hydroxyl number of less than 20.

10. A pharmaceutical preparation according to claim 6 wherein the semi-synthetic glycerides (b) have an iodine number of less than 3, and a hydroxyl number of less than 20.

11. A pharmaceutical preparation according to claim 1, wherein the saturated hydrocarbons (c) are present in an amount of 2-5.5 percent by weight, relative to the total weight of the pharmaceutical composition.

12. A pharmaceutical preparation according to claim 6, wherein the saturated hydrocarbons (c) are present in an amount of 2-5.5 percent by weight, relative to the total weight of the pharmaceutical composition.

* * * * *